United States Patent [19]

Royds et al.

[11] Patent Number: 5,466,465
[45] Date of Patent: Nov. 14, 1995

[54] TRANSDERMAL DRUG DELIVERY SYSTEM

[75] Inventors: Robert B. Royds, Plainsboro, N.J.; John Lim, Newtown; Joel D. Rosen, Langhorne, both of Pa.

[73] Assignee: Harrogate Holdings, Limited, Hamilton, Bermuda

[21] Appl. No.: 176,396

[22] Filed: Dec. 30, 1993

[51] Int. Cl.$^6$ ............................................. A61F 13/00
[52] U.S. Cl. .................... 424/449; 424/447; 424/448; 424/489; 604/41
[58] Field of Search ...................... 424/447–449

[56] References Cited

U.S. PATENT DOCUMENTS

| | | | |
|---|---|---|---|
| 4,314,557 | 2/1982 | Chandrasekaren | 424/449 |
| 4,379,454 | 4/1983 | Campbell et al. | 424/448 |
| 4,409,206 | 10/1983 | Stricker | 424/444 |
| 4,439,199 | 3/1984 | Amkraut et al. | 424/88 |
| 4,460,372 | 7/1984 | Campbell et al. | 424/449 |
| 4,484,923 | 11/1984 | Amkraut et al. | 424/88 |
| 4,597,961 | 7/1986 | Etscorn | 424/448 |
| 4,624,665 | 11/1986 | Nuwayser | 424/449 |
| 4,645,502 | 2/1987 | Gale et al. | 424/448 |
| 4,666,441 | 5/1987 | Andriola et al. | 424/448 |
| 4,690,683 | 9/1987 | Chien et al. | 424/448 |
| 4,708,716 | 11/1987 | Sibalis | 604/20 |
| 4,725,263 | 2/1988 | McNichols et al. | 604/20 |
| 4,736,866 | 4/1988 | Leder et al. | 436/6 |
| 4,743,249 | 5/1988 | Loveland | 424/447 |
| 4,749,574 | 6/1988 | Ueda et al. | 424/448 |
| 4,781,924 | 11/1988 | Lee et al. | 424/449 |
| 4,824,676 | 4/1989 | Bodor | 424/449 |
| 4,837,027 | 6/1989 | Lee et al. | 424/449 |
| 4,877,612 | 10/1989 | Berger et al. | 424/92 |
| 4,897,355 | 1/1990 | Eppstein et al. | 435/240.2 |
| 4,911,707 | 3/1990 | Heiber | 424/449 |
| 4,917,688 | 4/1990 | Nelson | 604/306 |
| 4,946,787 | 8/1990 | Eppstein et al. | 435/240.2 |
| 4,956,355 | 10/1990 | Prendergast | 514/178 |
| 4,963,367 | 10/1990 | Ecanow | 424/485 |
| 4,973,708 | 11/1990 | Digenis et al. | 548/544 |
| 4,994,278 | 2/1991 | Sablotsky et al. | 424/449 |
| 5,003,098 | 3/1991 | Siren et al. | 558/155 |
| 5,008,111 | 4/1991 | Bodor | 424/449 |
| 5,032,402 | 7/1991 | Digenis et al. | 424/448 |
| 5,049,386 | 9/1991 | Eppstein et al. | 424/427 |
| 5,050,612 | 9/1991 | Matsumara | 128/670 |
| 5,149,538 | 9/1992 | Granger et al. | 424/449 |
| 5,166,219 | 11/1992 | Katz | 514/724 |
| 5,194,451 | 3/1993 | Katz | 514/724 |
| 5,208,036 | 5/1993 | Eppstein et al. | 424/450 |
| 5,223,261 | 6/1993 | Nelson et al. | 424/443 |
| 5,230,897 | 7/1993 | Griffin et al. | 424/449 |
| 5,230,898 | 7/1993 | Horstmann et al. | 424/449 |
| 5,234,690 | 10/1993 | Chiang et al. | 424/448 |

*Primary Examiner*—D. Gabrielle Phelan
*Attorney, Agent, or Firm*—Robert C. Podwil; Reed Smith Shaw & McClay

[57] ABSTRACT

In a transdermal drug delivery system, encapsulation material used to coat drug granules controls the release of an active ingredient. The active ingredient is released into a water retaining matrix, which acts as a reservoir, and transdermal drug penetration is driven by the resulting concentration gradient. The delivery system is enclosed in a patch comprising a composite shell, which acts as an occlusive covering when attached to skin, thus enhancing the hydration of the skin area and fostering absorption of the drug. Visible change indicators incorporated into the system provide indicators at significant "landmarks" in the lifetime of the patch. Microcapsules used for the indicator may be formulated so that the penetration of moisture effects a color change at a time when the active ingredient is almost exhausted. This feature alerts to the user to the need for application of a replacement patch.

16 Claims, 4 Drawing Sheets

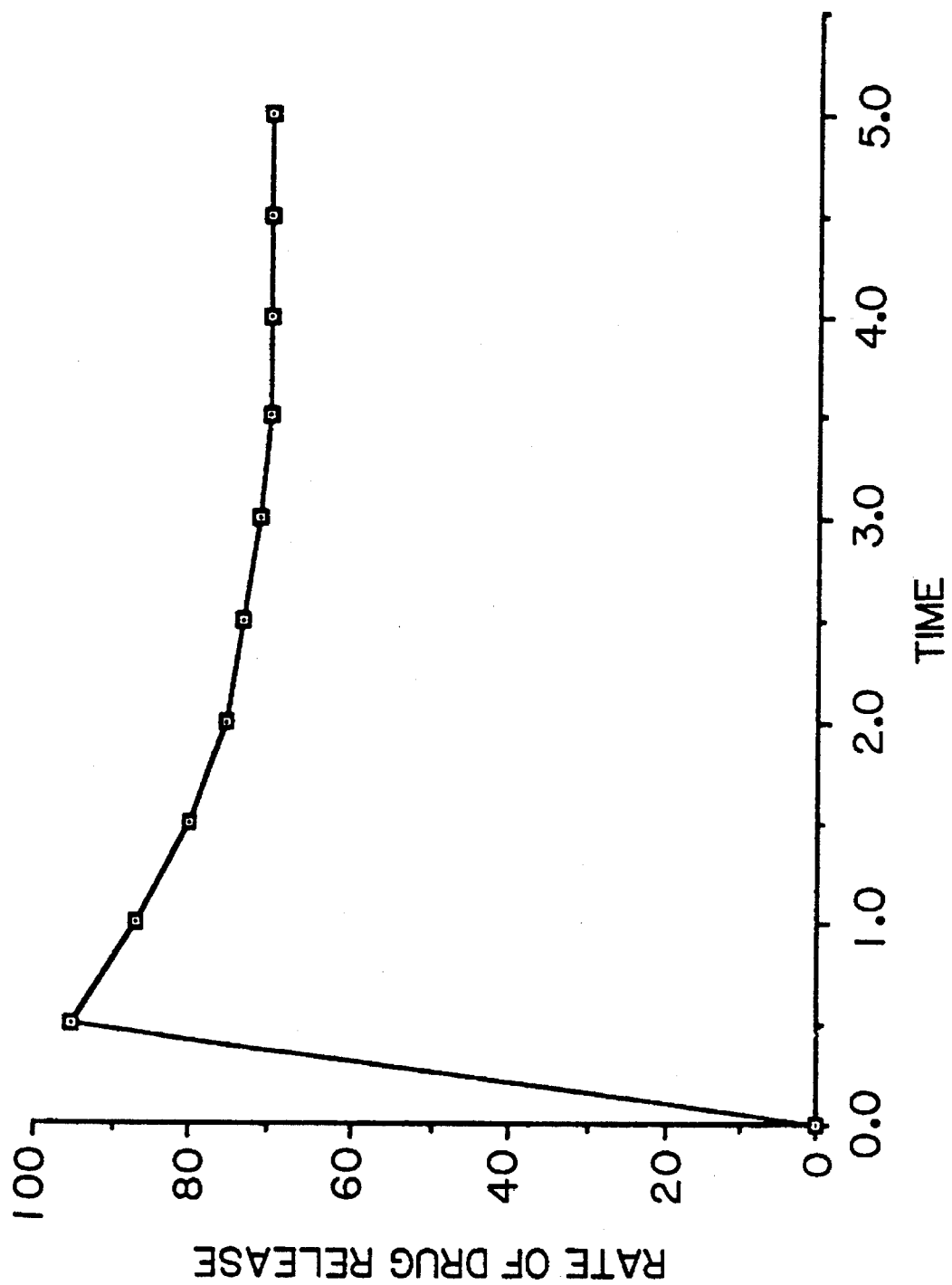

TRANSDERMAL DRUG DELIVERY SYSTEM

FIELD OF INVENTION

This invention relates to a transdermal drug delivery system, and more particularly, to a drug delivery system in which drug granules are encapsulated within material which controls the release over time of an active ingredient. In accordance with the invention, the active ingredient is released into a water retaining matrix.

BACKGROUND OF THE INVENTION

Devices and methods have been developed for the administration of pharmaceuticals at desired sustained levels by absorption through the skin. Transdermal delivery systems are available, or have been proposed, for many pharmaceutical agents. Typically, devices used in such techniques (often referred to as "patches") are attached to the skin of a patient, usually adhesively. The active agent is caused to diffuse from the device through the skin for absorption into the bloodstream. Upon absorption into the bloodstream, the agent is carried throughout the body of the patient.

Numerous techniques have been proposed to control the rate of release of pharmaceutical agents in transdermal delivery systems. For example, in U.S. Pat. Nos. 4,314,557 and 4,460,472, systems are disclosed which control the rate of release of an agent by the rate of which a drug solute phase dissolves in a polymer matrix phase. In U.S. Pat. No. 4,379,454, a drug and an absorption enhancer are said to be contained in a solid, semi-solid or gel matrix phase.

U.S. Pat. No. 4,409,206 describes a transdermal release system using a skin-compatible polyacrylate, which swells with water and may contain a hydrophilic component to regulate the rate of release.

U.S. Pat. No. 4,624,665 suggests sealing the skin with an occlusive layer, and transporting a desired dosage of an active agent across the layer from a rate controlling system.

U.S. Pat. No. 4,645,502 discloses an encapsulated permeation enhancer and a dry active agent within an aqueous gelled reservoir.

U.S. Pat. No. 4,690,683 discloses an active pharmaceutical dispersed in a polymeric material to form, by cross-linking, a matrix. As an alternative, a solution of the active pharmaceutical may be dispersed in the matrix prior to cross-linking, in which case, the patent says, "micro reservoirs" of the drug are formed in the matrix. A suggestion is also made in this patent of the possibility of incorporating a buffering agent into the matrix.

U.S. Pat. No. 5,149,538, discloses inclusion, in a transdermal delivery system for opioids, of an encapsulated antagonist as a control on the rate of delivery of the opioid.

BRIEF SUMMARY OF THE INVENTION

The drug delivery system of the present invention takes the form of an occlusive patch, which can be applied to a clean section of skin. The occlusion entraps sweat which in turn serves to hydrate the skin (specifically, the *stratum corneum*), thus facilitating drug penetration across the skin. The entrapped sweat can also saturate a matrix in which a specific drug is dispersed in microencapsulated form. The matrix is formulated from gums and gelling agents, so that it absorbs several times its own weight in moisture.

Drug release from the microcapsules into the matrix depends on the relative ease with which water from the entrapped sweat is able to penetrate the microcapsules' coat to dissolve drug in the inner core.

This process can be closely controlled by selection of the coating material for the drug, or by manipulating the constituents of the coating material. For example, the hydrophilic and hydrophobic elements of the coating material can be designed to affect the water permeability of the coating. Dissolved drug then leaches into the matrix and is delivered through the skin to exert the desired effect.

The present invention also includes a visible indicator, for example, microencapsulated color change indicator, which can be designed, through its formulation, to effect a visible change at significant time points in the lifetime of the patch. Since the mechanism effecting the visible change has a commonality or interrelatedness to that responsible for the release of drug, the manufacture of the indicator can be tailored to represent the status of drug release from the microcapsules. For example, the release of sufficient drug quantity to exert a therapeutic action can be associated with one visible change, and the near exhaustion of drug reserves from the microencapsulated core can be associated with a second visible change. This second feature, in particular, can serve as an indication to the user that a replacement patch should be applied. At present, only drugs intended for a prolonged duration of action (i.e., those requiring a sustained release profile) are administered via the transdermal route. This may be due, in part, to the inability to define precisely the quantity and extent of transdermal drug delivery in the short and intermediate terms. The use of indicators with transdermal drug delivery systems in accordance with the present invention, broadens the utility of drug delivery through the skin by allowing precise accurate indication and evaluation of the process of drug release, and thus the subsequent link to the desired therapeutic activity. This invention, therefore, facilitates exploitation of the transdermal route, where drugs are to be administered through the skin for short or intermediate durations of action, or in controlled release.

The above-mentioned visible indicator preferably comprises, for example, a layer of microencapsulated colored material visible through the backing of the patch.

The indicator may advantageously be designed as a system of multiple colored indicators, to represent the significant time points in the process of drug release from the microcapsules. For example, one indicator can be engineered to change color when a sufficient quantity of drug, determined to be necessary to initiate therapeutic action, has been released from the microcapsules. In a different embodiment, the indicator can be engineered to change color when the drug reserves in the microcapsules have been depleted, thus providing an easily interpreted visual cue to the useful lifetime of the patch. The design of the indicator makes it a particularly suitable model for the process of drug release, since the mechanism responsible for the drug release over time can be engineered to be the same as the release rate responsible for the indicator's visible change.

The present transdermal drug delivery system may be useful and advantageous in several settings:

In a preferred embodiment, a system in accordance with this invention can be used to deliver drugs such as, for example, quinine derivatives or pyrimethamine, in chemoprophylaxis against malaria. Children, for example, may prefer transdermal medication to the alternative of regular oral medication, and the effectiveness of transdermal medication is not compromised by the presence of concomitant illnesses and symptoms such as vomiting or diarrhea. Moreover, the present system can be engineered to release an antimalarial drug in a "zero order" fashion so that a constant, stable blood concentration can be maintained, thus reducing the likelihood of "breakthrough" infection from fluctuations in blood antimalarial concentration. The useful lifetime of the patch can readily be assessed, since the color indicator will change as drug is exhausted.

In another preferred embodiment, the system of this invention can be used to deliver analgesic drugs for example, in peri-operative and post-operative analgesia. The medical literature has shown that the need for postoperative pain relief is diminished when analgesics are administered to patients in the pre- or peri-operative period. Analgesics (for example, members of the class of non-steroidal anti-inflammatory drugs, such as flurbiprofen) may be formulated into a transdermal patch for application immediately prior to simple surgical or dental procedures. These patches will be left on the patient for continuing pain relief after the procedure. Such an application reduces the need for parenterally or orally administered pain relief. Furthermore, transdermal absorption of the analgesic agent will be unaffected by post operative vomiting, or by the absence of food in the gastrointestinal tract (for example, if the patient should have to undergo a preoperative fast). Further uses could include long-term use for chronic and sub-chronic painful and inflammatory conditions.

In yet another preferred embodiment, the system of this invention can be used to deliver topical doses of local anesthetic agents prior to minor surgical procedures or before the insertion of intravenous cannulae. Local anesthesia in this manner may be of particular advantage where subcutaneous or intradermal injections are a relative contraindication (for example, where such injections will distort the structure of underlying tissue and lead to an increase in scarring). In such a setting, patches can be applied by the patient, a relative or friend, or by a health professional in advance of the procedure. Multiple color indicators can then be designed to change with significant time landmarks. For example, one indicator may be used to signify when adequate quantities of local anesthetic should have been released to effect pain relief, and another indicator may signify when most of the dose has been delivered from the patch.

In still another preferred embodiment, the system of this invention is useful where constant levels of an antibiotic drug are desirable to prevent or treat recurrent or persistent infections; for example, for the delivery of anti-tuberculous drugs where sustained therapy is indicated. A patch containing a drug such as trimethoprim can also be designed to deliver effective levels of the drug to prevent the recurrence of urinary tract infections. This principle is also applicable for protecting susceptible patients (for example, those with a history of rheumatic heart disease) from the risk of heart valve damage from *Streptococcus spp.* following surgical or dental instrumentation. In this setting, a patch containing a suitable antibiotic drug will be applied immediately before the procedure, and then maintained for an appropriate length of time afterwards, so that a constant level of the drug will be present during the period of risk. Specific design of the indicator to change color as the drug reserves are depleted should minimize the likelihood of sub-optimal drug delivery, and result in successful eradication of the pathogenic microbes, or prophylaxis therefrom.

In another embodiment, the system can be designed as a reliable means of delivering drugs to treat patients with central nervous system deficits, for example the anti-psychotic drugs or medications to manage Alzheimer's disease. The application of a transdermal therapeutic system is easily supervised by a family member or a care provider who need not have a healthcare background. The patch does not require the patient to remember special instructions or to undertake complicated procedures for therapy maintenance, and the color indicators will be useful as a means to assess patient compliance and to assure dose delivery. (For example, if the patch is removed from the skin for any length of time, the indicator's color change would not be observed at the appointed time, and should prompt further investigation.)

BRIEF DESCRIPTION OF THE DRAWINGS

There are shown in the drawings forms of the inventions which are presently preferred, although it should be understood that the invention may be embodied in other specific forms without departing from its essential attributes.

FIG. 4 is a graph depicting the rate of drug release versus time for a patch designed for a combination release characteristic (i.e., initially rapid, followed by a sustained release profile).

Figure 1:
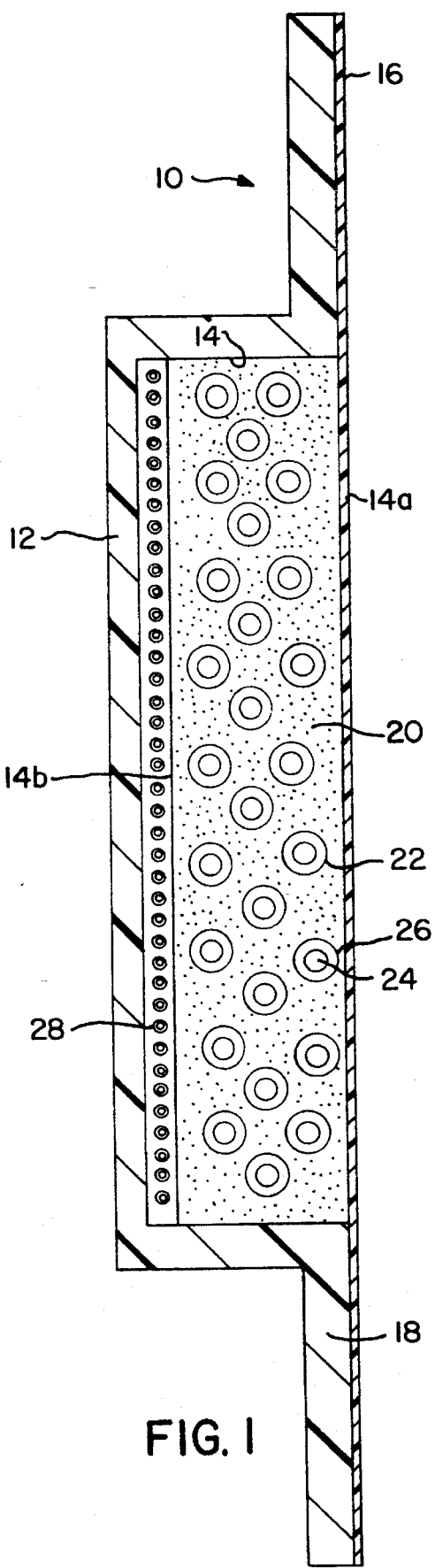
FIG. 1 is a schematic side elevation view, in cross-section, showing the structure of a drug delivery system in accordance with the invention.

Referring now to the drawings in detail, there is seen in FIG. 1 a transdermal patch, designated generally by the reference numeral 10. The patch 10 comprises a translucent water-impermeable shell, or backing layer 12. The shell 12 provides a reservoir 14 for the other components of the system, described below. In a presently preferred form of the invention, the shell 12 may be made of a plastic composite, formed by any suitable technique. Other suitable materials, generally of plastic polymeric composition, may be used for the shell 12, and will occur to those skilled in the art. The reservoir 14 may be said to have first and second faces 14a and 14b, the purpose of which is explained below.

A layer 16 of suitable pressure-sensitive adhesive material, of a conventional type, is disposed around a flange portion 18 of the shell, and enables the flange portion 18 to be secured to the skin of a user of the patch 10. It will be understood that when the patch 10 is provided to a user, the adhesive layer 16 will ordinarily be covered by a disposable protective layer, not shown.

When attached to the skin of a user, the shell 12 provides the above-mentioned occlusive covering, which enhances the hydration of the skin area covered by the patch 10. Hydration of the skin area, as will be explained, fosters release and absorption of the drug associated with the patch 10.

Within the reservoir 14 is a matrix, designated generally by the reference numeral 20. The matrix 20 is formulated to absorb several times its own weight in water, and may comprise, for example, guar, acacia or xanthan gum, or a gelling agent or polymer such as carboxypolymethylene, hydroxyethylcellulose or polyacrylamide. In the case of guar gum, for example, the matrix 20 can be made to absorb between five and ten times its own weight.

Within the matrix 20 in the illustrated form of the invention are microencapsulated particles of the drug. The drug microcapsules 22 in the illustrated embodiment include a core or granule 24 of active ingredient or ingredients (drugs), microencapsulated within a coating material 26. The sensitivity of the coating material to the permeation of moisture is controlled by the choice of coating material (for example, acrylate resins, or methylmetacrylic acid co-polymers), or by its formulation (for example, by incorporating different proportions of hydrophilic ethylcellulose derivatives and hydrophobic methylcellulose derivatives). Coatings 26 are selected or designed to be more or less susceptible to moisture penetration and subsequent drug core dissolution, according to the desired drug release characteristics. It will be understood that the dissolution of the drug enables it to leach into the matrix 20 for delivery to, and subsequent passage through, the skin of the user.

Figure 2:
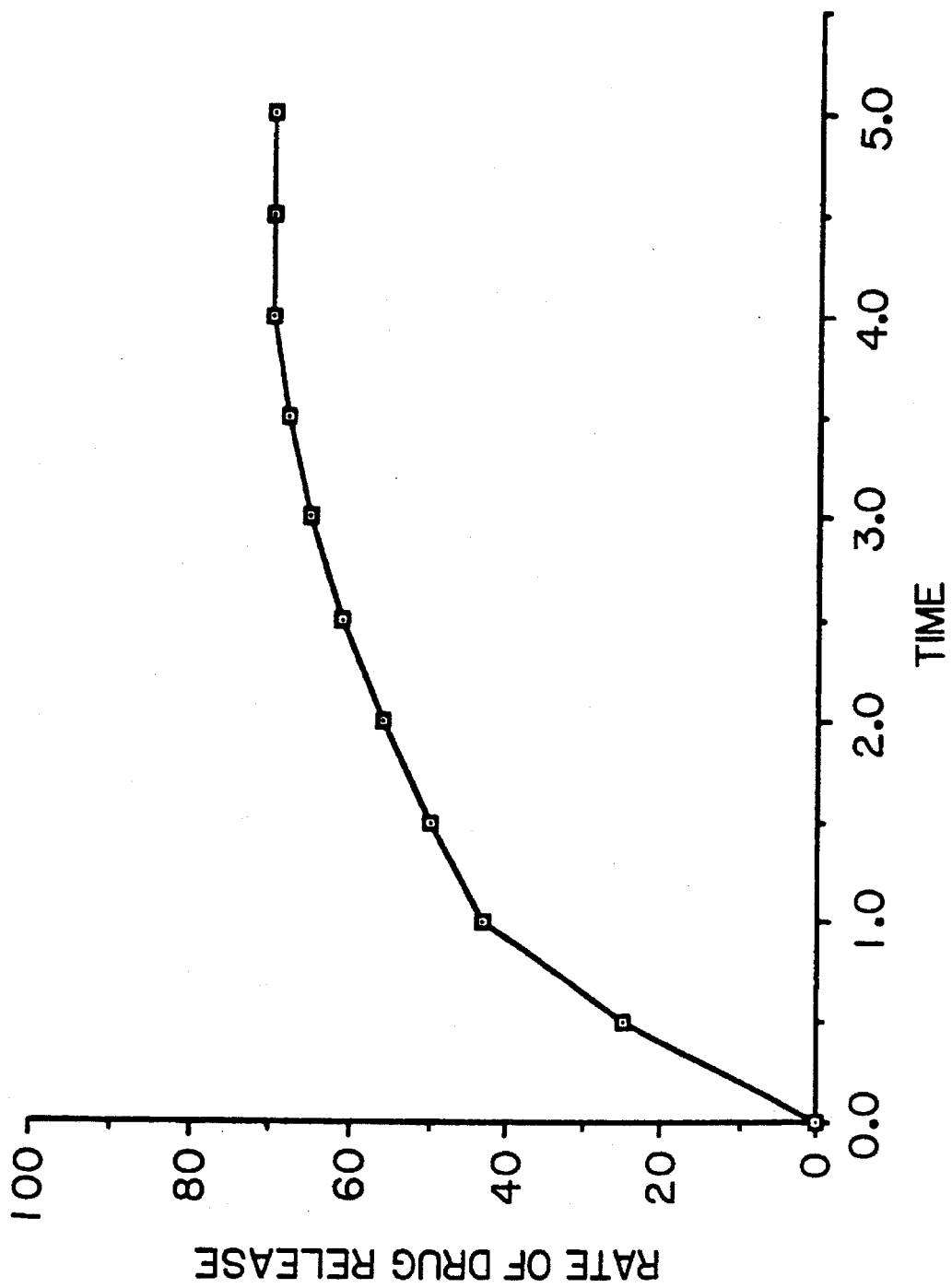
FIG. 2 is a graph depicting the rate of drug release versus time for a patch designed for slow and sustained release.
Figure 3:
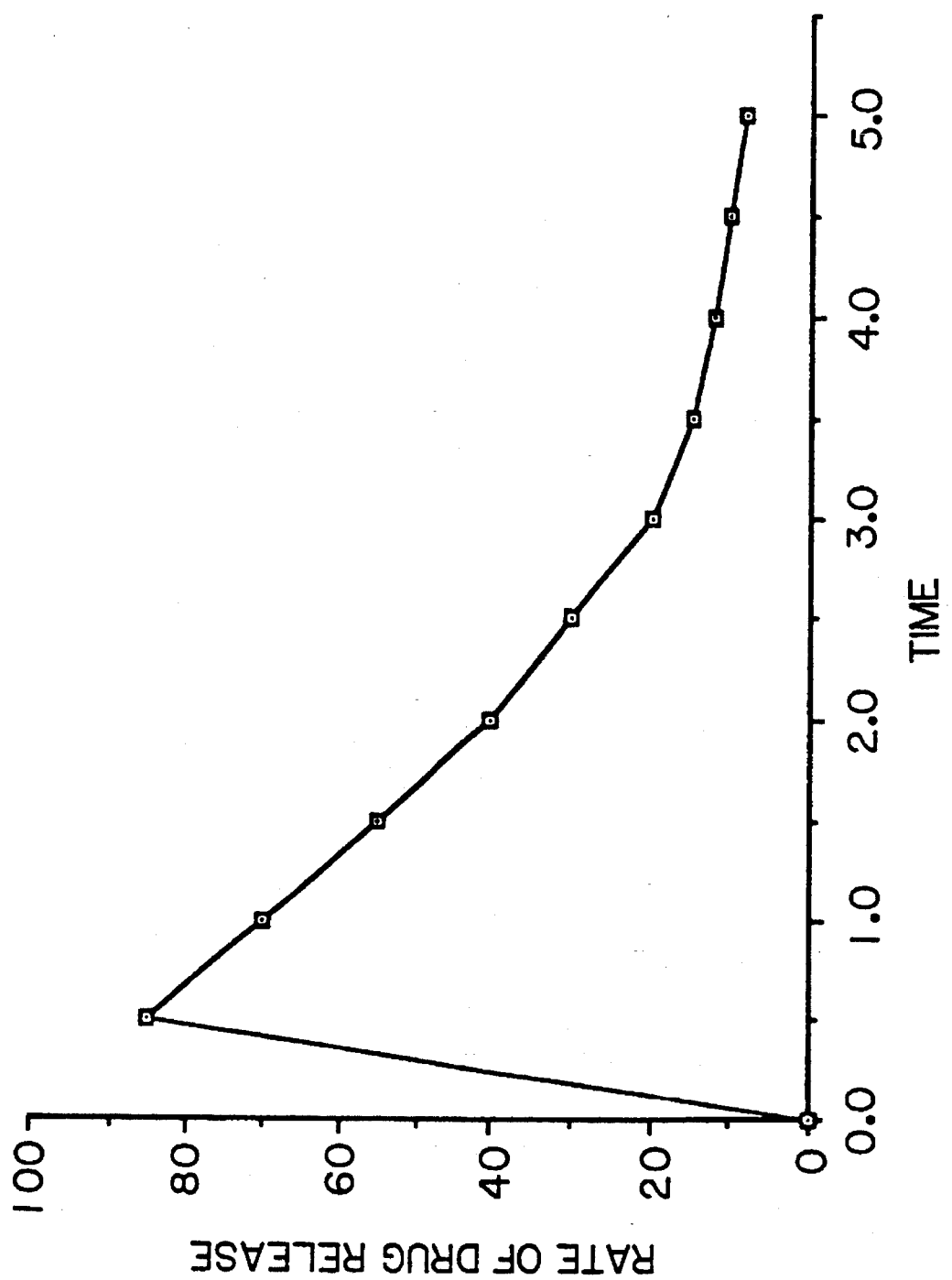
FIG. 3 is a graph depicting the rate of drug release versus time for a patch designed for rapid drug release.

It should now be apparent that judicious selection or manipulation of the microcapsule coating material 26 allows control of the rate of drug release from the core 24. A coating 26 that is relatively impervious to moisture, for example, one that is thicker or less permeable because of its physicochemical properties, or one that contains a higher content of hydrophobic elements in its composition, will result in a more gradual drug release over a sustained period. FIG. 2 depicts in graphical form a drug release profile for a patch designed for slow and sustained release. This type of release characteristic may be desired for maintaining stable concentrations of drugs for a prolonged duration, for example, in the chemoprophylaxis of malaria. In contrast, a coating 26 that is relatively permeable to water will rapidly release the drug over a short period. FIG. 3 depicts in graphical form a drug release profile for a patch designed for such rapid release. This may be the goal where the patch is intended to deliver a local anesthetic drug, when a rapid onset, and a subsequent rapid discontinuation of the biological effect is desired. A combination of both release characteristics may be useful in the appropriate setting, for example, in the patch for delivering a drug to effect peri- and post-operative analgesia, since the goal here is a rapid onset, followed by a sustained maintenance of pain relief. FIG. 4 depicts in graphical form a drug release profile for a patch of this type. A combination of both the initially rapid release followed by a sustained release profile can be achieved by the incorporation of different "populations" of microcapsules into the patch 10. (For example, microcapsules with coating materials of variable composition and having a variety of water permeability characteristics may be included in the formulation to provide the desired release characteristics).

Also provided within the reservoir 14 adjacent to and operatively associated with the face 14b, and visible through the patch backing, is a microencapsulated color indicator designated generally by the reference numeral 28. This indicator may be designed to change color in response to the presence of water, electrolyte or other secretion, and may be manufactured from inorganic salts that will change color with hydration (for example, anyhdrous copper sulfate or cobalt chloride). Alternatively, colorful dyes (like amaranth or mercurochrome) can be microencapsulted to effect a color change when released. The utility of such an indicator is that it exploits the common mechanism for activating both the indicator's color change and the process for drug release, namely, the ease with which water, electrolyte or other secretion penetrates the coating material of the microcapsules.

Commonality or interrelatedness of mechanism enables the color indicator to be tailored to accurately reflect the status of drug release from the microcapsules, either by an appropriate choice of coating material or by manipulation of the components in the coating. This feature is advantageous in instances where the timing of events such as the onset, peak, and decline of therapeutic effect is an important consideration in the proper use of the drug. For example, in designing a patch for the delivery of local anesthetic agent, a series of different color indicators can be fabricated to change color at time points corresponding to the time of onset of local anesthesia, the time of peak effect, and the time at which the anesthetic effect begins to wear off. The color changes that will indicate these important "landmarks" in the lifetime of the patch will very closely reflect the true status (i.e., the quantity and extent) of drug release from the drug microcapsules.

The commonality of mechanism as between the indicator and the drug release, also allows the color change to indicate that successful drug delivery has taken place. This feature will be useful in ensuring compliance to dosing instructions, since the color change will not be achieved without continued contact with the skin. Observation, therefore, that a color change did not occur at the expected time can prompt further investigation. Patches in accordance with this invention will have at least one indicator, designed to change color when the drug reserves within the microcapsules are almost exhausted. This feature is intended to prompt the user to discard the old patch and to apply a replacement patch, where required.

The above-described patches 10 may be used in conjunction with preparatory skin cleanser, containing, for example, alcohol and a weakly buffered acidic or basic solution. The solvent would serve to remove surface grease to eliminate a barrier to absorption at the skin, and a buffered acidic or basic solution may be selected according to the physical or chemical properties of the particular drug to be administered and to maximize drug stability and enhance transdermal penetration.

This invention includes the description of a microencapsulated color change indicator that can be designed, through its formulation, to effect a visible change at significant time points in the lifetime of the patch. Since the dynamics of the mechanism effecting the color change are related to that responsible for the release of drug, the manufacture of the color indicator can be tailored to represent the status of drug release from the microcapsules. For example, the release of sufficient drug quantity to exert a therapeutic action can be associated with one color change indicator, and the near exhaustion of drug reserves from the microencapsulated core can be associated with a second color change. This second feature, in particular, will serve as an indicator to the user that a replacement patch should be applied.

The present invention may be embodied in other specific forms without departing from its spirit or essential attributes. Accordingly, reference should be made to the appended claims rather than the foregoing specification, as indicating the scope of the invention.

We claim:

1. A drug delivery system for the delivery of a drug across the skin of a user comprising:

a shell, said shell providing an occlusive covering on the skin of the user to enhance the hydration of the skin, said shell comprising a reservoir having a first face and a second face, said reservoir having therein a matrix adapted to absorb moisture from the skin and hydrate the skin to facilitate penetration of the skin by a drug, said reservoir further having therein a plurality of microcapsules, said microcapsules being dispersed within said matrix and having contained therein an effective concentration of a drug and a coating formulated to be susceptible to penetration by moisture;

means on said first face of said reservoir for adhering said shell to the skin; and a visible indicator operatively associated with said second face of said reservoir, said indicator comprising a reagent formulated to visibly change in response to the presence of moisture, electrolytes or other secretions in said matrix, said visible indicator comprising a first indicator and at least a second indicator, said first indicator providing a first visible change indicative of a first event in relation to delivery of said drug, and said second indicator providing a second visible change indicative of a second event in relation to delivery of said drug.

2. A delivery system in accordance with claim 1, wherein said visible indicator is a color indicator, said indicator comprising a plurality of microparticles permeable to moisture and having contained therein a chemical intermediate adapted to absorb moisture from said matrix and to irreversibly change color in response to the moisture level in said matrix.

3. A delivery system in accordance with claim 2, wherein said microscapsules are uniformly dispersed within said matrix.

4. A delivery system in accordance with claim 2 wherein said drug containing-microcapsules are so constructed as to control the rate of release of said drug into said matrix.

5. A delivery system in accordance with claim 4, wherein said chemical intermediate containing-microparticles are so constructed as to control the rate of absorption of said moisture.

6. A delivery system in accordance with claim 5, wherein said color change is indicative of the release of said drug from said microcapsules and the depletion of said drug from said microcapsules.

7. A delivery system in accordance with claim 6, wherein said color change is indicative of the lifetime of said system.

8. A delivery system in accordance with claim 7, wherein said matrix is adapted to absorb moisture from the skin several times the weight of said matrix.

9. A delivery system in accordance with claim 8, wherein said matrix is selected from the group consisting of guar, acacia, xantham gums.

10. A delivery system in accordance with claim 8, wherein said matrix is selected from the group consisting of a gelling agent selected from the group consisting of carboxypolymethylene, hydroxyethylcellulose and polyacrylamide.

11. A delivery system in accordance with claim 8, wherein said drug is adapted for the chemoprophylaxis of malaria.

12. A delivery system in accordance with claim 8, wherein said drug comprises an analgesic for use in peri-operative and post-operative pain relief.

13. A delivery system in accordance with claim 8, wherein said system is adapted for the topical delivery of anesthetic agents.

14. A delivery system in accordance with claim 8, wherein said drug comprises an antibiotic agent.

15. A delivery system in accordance with claim 8, wherein said drug comprises medication for treating the central nervous system deficits.

16. A delivery system in accordance with claim 1, wherein said visible indicator comprises a first indicator and a series of subsequent indicators, said first indicator providing a first visible change indicative of a first event in relation to delivery of said drug, and each subsequent indicator providing a visible change indicative of a respective subsequent event in relation to delivery of said drug.

* * * * *